(12) United States Patent
Holtwick

(10) Patent No.: US 9,375,562 B2
(45) Date of Patent: Jun. 28, 2016

(54) FLEXIBLE VALVE GEOMETRY FOR THE USE OF RIGID MATERIALS

(75) Inventor: Marc Holtwick, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 41 days.

(21) Appl. No.: 14/115,621

(22) PCT Filed: May 4, 2012

(86) PCT No.: PCT/EP2012/058255
§ 371 (c)(1),
(2), (4) Date: Nov. 4, 2013

(87) PCT Pub. No.: WO2012/152695
PCT Pub. Date: Nov. 15, 2012

(65) Prior Publication Data
US 2014/0081217 A1    Mar. 20, 2014

(30) Foreign Application Priority Data

May 6, 2011   (EP) ..................... 11165118

(51) Int. Cl.
| | | |
|---|---|---|
| *A61M 5/19* | (2006.01) | |
| *A61M 5/24* | (2006.01) | |
| *A61M 39/24* | (2006.01) | |
| *A61M 5/168* | (2006.01) | |
| *F16K 15/14* | (2006.01) | |
| *A61M 5/145* | (2006.01) | |

(52) U.S. Cl.
CPC .......... *A61M 39/24* (2013.01); *A61M 5/16827* (2013.01); *A61M 5/19* (2013.01); *A61M 5/2448* (2013.01); *A61M 5/2459* (2013.01); *F16K 15/145* (2013.01); *A61M 5/1452* (2013.01); *A61M 2039/246* (2013.01); *Y10T 137/7895* (2015.04)

(58) Field of Classification Search
CPC .......... A61M 39/24; A61M 2039/242; A61M 2039/2406; A61M 2039/2433; A61M 2039/2466; A61M 2039/2446; A61M 5/16827; A61M 5/1452; A61M 5/2448; A61M 5/19; A61M 5/2459; F16K 15/145; F16K 15/148; F16K 15/185; F16K 15/021
See application file for complete search history.

(56) References Cited

U.S. PATENT DOCUMENTS

| | | | | |
|---|---|---|---|---|
| 4,109,653 | A * | 8/1978 | Kozam ..................... | A61C 5/02 604/191 |
| 5,147,323 | A * | 9/1992 | Haber et al. ................... | 604/191 |
| 5,240,146 | A * | 8/1993 | Smedley et al. ............... | 222/137 |
| 5,305,795 | A * | 4/1994 | Forberg ......................... | 137/859 |
| 5,465,938 | A * | 11/1995 | Werge et al. ................. | 251/149.1 |
| 5,484,880 | A * | 1/1996 | Yamashita et al. ............ | 528/353 |
| 5,503,538 | A |  4/1996 | Wiernicki et al. | |

(Continued)

FOREIGN PATENT DOCUMENTS

| | | |
|---|---|---|
| DE | 202006001475 U1 | 4/2006 |
| EP | 0247824 A2 | 12/1987 |

(Continued)

*Primary Examiner* — Andrew Gilbert
(74) *Attorney, Agent, or Firm* — McDonnell Boehnen Hulbert & Berghoff LLP

(57) ABSTRACT

The present invention inter-alia relates to an apparatus comprising a diaphragm valve, wherein a diaphragm of said diaphragm valve is made from a substantially rigid material, having at least partially an flexible cross-sectional shape.

15 Claims, 14 Drawing Sheets

(56) References Cited

U.S. PATENT DOCUMENTS

| | | | |
|---|---|---|---|
| 5,505,704 A | 4/1996 | Pawelka et al. | |
| 5,725,019 A | 3/1998 | Kohlstadt | |
| 5,771,935 A * | 6/1998 | Myers | 137/859 |
| 6,142,062 A * | 11/2000 | Streitman | 92/99 |
| 6,165,154 A * | 12/2000 | Gray | A61M 5/16809 604/153 |
| 6,230,609 B1 * | 5/2001 | Bender et al. | 92/99 |
| 6,390,120 B1 * | 5/2002 | Guala | 137/512.15 |
| 6,537,258 B1 * | 3/2003 | Guala | 604/247 |
| 6,685,164 B1 * | 2/2004 | Koizumi et al. | 251/331 |
| 2004/0102738 A1 * | 5/2004 | Dikeman et al. | 604/256 |
| 2005/0194047 A1 * | 9/2005 | Bausmith, III | 137/512 |
| 2009/0060750 A1 * | 3/2009 | Chen et al. | 417/26 |
| 2014/0005603 A1 * | 1/2014 | Holtwick | A61M 5/16813 604/110 |
| 2014/0046267 A1 * | 2/2014 | Holtwick | A61M 5/19 604/191 |
| 2014/0054295 A1 * | 2/2014 | Holtwick | A61M 5/19 220/502 |

FOREIGN PATENT DOCUMENTS

| | | |
|---|---|---|
| EP | 1099456 A1 | 5/2001 |
| EP | 2283885 A1 | 2/2011 |
| JP | 200957963 A | 3/2009 |
| WO | 9318806 A1 | 9/1993 |
| WO | 9422507 A2 | 10/1994 |

* cited by examiner

FLEXIBLE VALVE GEOMETRY FOR THE USE OF RIGID MATERIALS

CROSS REFERENCE TO RELATED APPLICATIONS

The present application is a U.S. National Phase application pursuant to 35 U.S.C. §371 of International Application No. PCT/EP2012/058255 filed May 4, 2012, which claims priority to European Patent application No. 11165118.8 filed May 6, 2011. The entire disclosure contents of these applications are herewith incorporated by reference into the present application.

FIELD OF INVENTION

The present patent application relates to medical devices of delivering at least two drug agents from separate reservoirs. Such drug agents may comprise a first and a second medicament. The medical device includes a dose setting mechanism for delivering the drug automatically or manually by the user.

BACKGROUND

The drug agents may be contained in two or more multiple dose reservoirs, containers or packages, each containing independent (single drug compound) or pre-mixed (co-formulated multiple drug compounds) drug agents.

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

SUMMARY

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then only combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with the primary reservoir and with a secondary reservoir of medicament containing at least one drug agent. The drug dispense interface can be a type of outlet that allows the two or more medicaments to exit the system and be delivered to the patient.

The combination of compounds as discrete units or as a mixed unit can be delivered to the body via a double-ended needle assembly. This would provide a combination drug injection system that, from a user's perspective, would be achieved in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable.

5. Optionally, after the second dose has been computed, the device may be placed in an armed condition. In such an optional armed condition, this may be achieved by pressing and/or holding an "OK" button on a control panel. This condition may provide for greater than a predefined period of time before the device can be used to dispense the combined dose.

6. Then, the user will insert or apply the distal end of the dose dispenser (e.g., a double ended needle assembly) into the desired injection site. The dose of the combination of the primary compound and the secondary compound (and potentially a third medicament) is administered by activating an injection user interface (e.g., an injection button).

Both medicaments may be delivered via one injection needle or dose dispenser and in one injection step. This offers a convenient benefit to the user in terms of reduced user steps compared to administering two separate injections.

To prevent cross contamination and back flow of the first and second medicaments contained in the first and second reservoirs, respectively, the dispense interface may comprise a valve arrangement, preferably a small-size valve arrangement.

Preferably diaphragm valves are used in this valve arrangement, because diaphragm valves inter-alia have a low opening pressure threshold, give minimal resistance to flow when open and seal effectively against back pressure. For instance, in such a dispense interface, the opening pressure threshold of the diaphragm valve is preferably low to prevent a leakage of the fluid connections to the medical device and/or the dose dispenser.

Furthermore, diaphragm valves can be designed to be very small.

The diaphragm of these diaphragm valves is made from soft materials (e.g. sealing beads) such as rubbery-elastic materials such as thermoplastic elastomers or liquid silicone rubbers. Therein, a plasticizer is contained in the soft material to obtain a diaphragm with the necessary flexibility. For instance, this flexibility may inter-alia be necessary to provide a diaphragm valve having a low opening pressure threshold, giving minimal resistance to flow when open and/or sealing effectively against back pressure. However, soft materials and, in particular, soft materials containing plasticizers such as thermoplastic elastomers or liquid silicone rubbers are problematic in terms of biocompatibility. For instance, plasticizers contained in injection-mouldable soft materials are specifically problematic in terms of biocompatibility.

Since diaphragms may at least partially be in (permanent) contact with the medicament, they are preferably made from biocompatible materials. For instance, plasticizers contained in a diaphragm may contaminate the medicament.

Therefore, the present invention inter-alia faces the technical problem of providing a biocompatible diaphragm for a diaphragm valve such as a diaphragm valve used in a valve arrangement of a dispense interface.

According to the present invention, an apparatus comprises a diaphragm valve, wherein a diaphragm of the diaphragm valve is made from a substantially rigid material, having at least partially a flexible cross-sectional shape.

The apparatus may be a drug delivery device such as a medical device configured to eject a drug agent (e.g. a dose of a medicament) such as an infusion device or an injection device, for instance an insulin injection pen. Injection devices may be used either by medical personnel or by patients themselves. As an example, type-1 and type-2 diabetes may be treated by patients themselves by injection of insulin doses, for example once or several times per day.

For instance, the apparatus is a medical device configured to eject at least two drug agents from separate reservoirs comprising a first and a second medicament, respectively, but it is not limited thereto. Alternatively, the medical device is for instance a conventional medical device configured to eject a drug agent from a single reservoir such as Applicant's Solostar insulin injection pen.

Alternatively, the apparatus may be a disposable part attachable to a medical device such as a drug delivery device. For instance, the apparatus is a dispense interface attachable to a medical device configured to eject a drug agent. A dispense interface may be configured to be in fluid communication with at least one reservoir of the medical device containing at least one medicament. For instance, the dispense interface is a type of outlet that allows the at least one medicament to exit the medical device.

The diaphragm valve may comprise a valve body and the diaphragm. The valve body may comprise a valve chamber and an inlet and an outlet port of the valve chamber. For instance, the inlet port is arranged at a sidewall of the valve chamber. The inlet port may be in fluid communication with a reservoir containing a fluid such as a reservoir of the medical device. The outlet port of the valve chamber may be arranged at a convex protrusion of the valve chamber, wherein the convex protrusion extends into the valve chamber. The outlet port may be in fluid communication with an outlet of the dispense interface. For instance, the inlet and/or the outlet port are respectively one of an end of a pierce needle, a start point of a fluid groove, a septum or the like.

The diaphragm may be arranged in the valve chamber such that the diaphragm provides a fluid seal between the inlet port and the outlet port. For instance, a protrusion at the center of the diaphragm is arranged in a valve cavity positioned in the center of the convex protrusion and the diaphragm separates the inlet port of the valve chamber from the outlet port of the valve chamber. In such an arrangement, the diaphragm provides a fluid seal between the inlet port and the outlet port, the diaphragm valve is closed.

For instance, the area of the surface of the convex protrusion oriented towards the diaphragm may be not less than the area of the surface of the diaphragm oriented towards the convex protrusion such that, if the diaphragm is inverted (e.g. put over the convex protrusion) and resides along the convex protrusion, the diaphragm valve does at least partially not cover the outlet port and does not provide a fluid seal between the inlet port and the outlet port, the diaphragm valve is opened and the diaphragm allows fluid flow from the inlet port to the outlet port.

As an example, the valve chamber may at least partially be formed from a circular recess and a cover. The inlet port may be arranged at this circular recess; and the outlet port and the convex protrusion is for instance arranged at this cover. The diaphragm or a rim of the diaphragm for instance resides on a circular set-back of the recess such that the diaphragm provides a fluid seal between the inlet port and the outlet port such that the valve is closed. For instance, the valve cavity of the convex protrusion of the cover may at least partially fix the center of the diaphragm in the valve chamber, for instance it presses the diaphragm or the rim of the diaphragm on the circular set-back of the recess such that the diaphragm initially sits in a pre-stressed state in the valve chamber.

If (fluidic) pressure is applied upon a surface of the diaphragm oriented towards the inlet port of the valve chamber, the diaphragm may change from the pre-stressed state to an even more stressed state (which is below referred to as stressed state), alternatively the diaphragm may change from an un-stressed state to the stressed state; and, if an opening pressure threshold is overcome, the diaphragm inverts and resides along the convex protrusion. The (fluidic) pressure may be increased by increasing the pressure in a fluid reservoir being in fluid communication with the inlet port. In the stressed state, the diaphragm may accordingly enable a fluid flow from the inlet port to the outlet port. The opening pressure threshold may advantageously correspond to a pressure of about 25 mBar to 200 mBar such as 50 mBar, 100 mBar or 150 mBar, but is not limited thereto.

However, if the (fluidic) pressure falls below a closing pressure threshold, the diaphragm may return to the initial shape and, accordingly, disables the fluid flow from the inlet port to the outlet port. Back pressure applied on the surface of the diaphragm oriented towards the outlet port of the valve chamber may for instance amplify the returning of the diaphragm to the initial-state.

The opening pressure threshold may relate to the stiffness of the diaphragm. Stiffness is to be understood to relate to the physical property of the diaphragm to resist to a (elastic) deformation by a stress.

The closing pressure threshold may relate to the elastic counterforce of the diaphragm in response to the inversion and/or to the elasticity of the diaphragm. Elasticity is to be understood to relate to the physical property of the diaphragm to return to the initial shape after a stress which made it (elastically) deform is (partially) removed.

The closing pressure threshold may be equal to the opening pressure threshold.

According to the present invention, the diaphragm is made from a substantially rigid material. Soft materials typically have a lesser biocompatibility than substantially rigid materials or rigid materials. In particular, soft materials have a higher likelihood to fail biocompatibility, as they often contain softeners.

For instance, the diaphragm is made from a substantially rigid and biocompatible material such as plastics which contain no or only less plasticizers or only biocompatible plasticizers. In particular, the diaphragm is made from an injection moldable material containing no or less plasticizers or only biocompatible plasticizers. As an example, the substantially rigid material is one of semi-crystalline thermoplastics, crystalline thermoplastics and amorphous thermoplastics.

The use of a substantially rigid material is inter-alia advantageous in order to improve the biocompatibility of the diaphragm.

However, the elasticity of the diaphragm made from a substantially rigid material may be decreased, for instance in comparison to a similarly shaped diaphragm made from a soft material such as a rubbery-elastic materials. For instance, the elastic limit of the substantially rigid material is less than the elastic limit of the soft material. This may cause a fracture or a non-reversible change of the shape of the diaphragm made from the substantially rigid material in response to stress.

Furthermore, the stiffness of the diaphragm made from a substantially rigid material may be increased, for instance in comparison to a similarly shaped diaphragm made from a soft material such as a rubbery-elastic materials. For instance, the young's modulus of the substantially rigid material is greater than the young's modulus of the soft material. Accordingly, the opening pressure threshold (i.e. the opening pressure threshold necessary to invert the diaphragm) may be also increased.

According to the present invention, the diaphragm has a flexible cross-sectional shape. For instance, a basic convex shape (e.g. a cup shape or a bowl shape) or basic disc shape of the diaphragm may be interrupted by the flexible cross-sectional shape. For instance, the flexible cross-sectional shape is arranged between a rim of the diaphragm and the center of the diaphragm.

The flexible cross-sectional shape of the diaphragm may be configured to decrease the stiffness of the diaphragm, for instance in comparison with a diaphragm having the same basic shape, made from the same material and having the same thickness such as an uninterruptedly convex shaped diaphragm (e.g. a cup shaped or bowl shaped diaphragm) or a disc shaped diaphragm (i.e. a diaphragm without the flexible cross-sectional shape). This is inter-alia advantageous in order to lower the opening pressure threshold. In particular, this is advantageous in order to allow the use of a diaphragm made from a substantially rigid material with a low opening pressure threshold.

Typically, a convex shaped diaphragm may be at least partially stiffer than a disc shaped diaphragm made from the same material and having the same thickness as the convex shaped diaphragm. For instance, a convex shaped diaphragm made from rigid material may be undesirably stiff in comparison to a disc shaped diaphragm, for instance a disc shaped diaphragm having a flexible cross-sectional shape.

The flexible cross-sectional shape may be configured to increase the elasticity of the diaphragm, for instance in comparison with a conventional diaphragm made from the same material and having the same thickness such as an uninterruptedly convex or disc shaped diaphragm (i.e. a diaphragm without the flexible cross-sectional shape). This is inter-alia advantageous in order to prevent a fracture or a non-reversible change of the shape of the diaphragm in response to stress. In particular, this is advantageous in order to allow the use of a diaphragm made from a substantially rigid material.

In the following, features and embodiments (exhibiting further features) of the present invention will be described, which are understood to apply to the apparatus as described above. These single features/embodiments are considered to be exemplary and non-limiting, and to be respectively combinable independently from other disclosed features/embodiments of the apparatus as described above. Nevertheless, these features/embodiments shall also be considered to be disclosed in all possible combinations with each other and with the apparatus as described above.

According to an embodiment of the present invention, the flexible cross-sectional shape is configured to decrease a second moment of area of the diaphragm. For instance, the thickness of the substantially rigid material is lowered along the flexible cross-sectional shape such that the stiffness of the diaphragm is decreased. This embodiment is inter-alia advantageous in order to lower the opening pressure threshold.

According to an embodiment of the present invention, a thickness of the substantially rigid material varies at least in the flexible cross-sectional shape. As described above, this embodiment is inter-alia advantageous in order to decrease a second moment of area of the diaphragm.

Alternatively or additionally, the density of the substantially rigid material may vary at least in the flexible cross-sectional shape. For instance, the density is lowered such that the stiffness of the diaphragm is decreased. This embodiment is inter-alia advantageous in order to lower the opening pressure threshold.

According to an embodiment of the present invention, the flexible cross-sectional shape is at least partially wavelike. The wavelike flexible cross-sectional shape may decrease the stiffness of the diaphragm. The wavelike flexible cross-sectional shape may increase the elasticity of the diaphragm. This embodiment is inter-alia advantageous in order to lower the opening pressure threshold and/or to prevent a fracture or a non-reversible change of the shape of the diaphragm in response to stress.

Alternatively or additionally, the flexible cross-sectional shape is at least partially "Z-shaped". The cross-sectional "Z-shape" is for instance arranged in a surface plane of the diaphragm. The "Z-shape" may be angled to a surface plane (e.g. 45°, 90° or 180°).

According to an embodiment of the present invention, the at least partially wavelike flexible cross-sectional shape comprises at least one through and/or one peak. For instance, the number of peaks and/or throughs and/or the amplitude thereof may correspond to the stiffness and/or to the elasticity of the diaphragm. The wavelike flexible cross-sectional shape may comprise one or more throughs and/or one or more peaks such as at least two throughs and two peaks.

As described above, this embodiment is inter-alia advantageous in order to lower the opening pressure threshold and/or to prevent a fracture or a non-reversible change of the shape of the diaphragm in response to stress.

According to an embodiment of the present invention, the diaphragm is substantially convex shaped. For instance, the inversion of an initially substantially convex shaped diaphragm residing along the convex protrusion is more intense than the inversion of a disc shaped diaphragm made from the same material and having the same thickness. Accordingly, the elastic counterforce in response to the inversion of the substantially convex shaped diaphragm is higher and the closing pressure threshold is lowered.

This embodiment is inter-alia advantageous in order to decrease the closing pressure threshold of the diaphragm.

Furthermore, a substantially convex shaped diaphragm may seal more effectively against back pressure (i.e. pressure applied upon the surface of the diaphragm oriented towards the outlet), for instance in comparison to a substantially disc shaped diaphragm.

According to an embodiment of the present invention, the diaphragm is rotationally symmetric. This embodiment is inter-alia advantageous to enable a symmetric behavior of the diaphragm, for instance a symmetric inversion in response to stress.

According to an embodiment of the present invention, the flexible cross-sectional shape is arranged between a rim of the diaphragm and a center of the diaphragm. For instance, if the diaphragm valve is closed, the rim of the diaphragm may engage with a circular notch or reside on a circular setback of the valve chamber to provide an effective fluid seal between the inlet port and the outlet port and/or to effectively seal against back pressure.

According to an embodiment of the present invention, an outer diameter of the diaphragm is equal to or less than 1 cm. In particular, the outer diameter may be equal to or less than 5 mm (e.g. 4 mm or 3 mm). This embodiment is inter-alia advantageous in order to provide a small-size diaphragm valve and to minimize the ullage volume of the valve and/or the apparatus.

According to an embodiment of the present invention, a young's modulus of the substantially rigid material is not less than 100 N/mm$^2$. In particular, the young's modulus of the substantially rigid material is not less than 200 N/mm$^2$ or 300 N/mm$^2$ or 1000 N/mm$^2$. This embodiment is inter-alia advantageous in order to allow to made the diaphragm from a substantially rigid and biocompatible material such as plastics which contain no or only less plasticizers.

According to an embodiment of the present invention, the substantially rigid material is one of semi-crystalline thermoplastics and amorphous thermoplastics. For instance, semi-crystalline thermoplastics and amorphous thermoplastics are substantially rigid and biocompatible materials. For instance, semi-crystalline thermoplastics typically have a young's modulus not less than 300 N/mm$^2$. For instance, amorphous thermoplastics typically have a young's modulus not less than 1000 N/mm$^2$. As described above, this embodiment is inter-alia advantageous in order to make the diaphragm from a biocompatible material.

According to an embodiment of the present invention, the substantially rigid material is one of low density polyethylene and polytetrafluoroethylene. For instance, low density polyethylene and polytetrafluoroethylene are biocompatible. Low density polyethylene and polytetrafluoroethylene may be injection moldable. This embodiment is inter-alia advantageous in order to make the diaphragm from a biocompatible material and to allow a cost-effective production of the diaphragm.

According to an embodiment of the present invention, the diaphragm valve is configured to enable fluid flow, if a fluidic pressure threshold is applied on the diaphragm valve.

As described above, if fluidic pressure is applied upon the surface of the diaphragm oriented towards the inlet part of the valve chamber, the diaphragm may change from the pre-stressed state to a stressed state; and if an opening pressure threshold is overcome, the diaphragm inverts and the diaphragm resides along the convex protrusion. In this stressed state, the diaphragm may accordingly enable a fluid flow from the inlet port to the outlet port. However, if the (fluidic) pressure falls below a closing pressure threshold, the diaphragm may return to the initial shape and disables the fluid flow from the inlet port to the outlet port.

This embodiment is inter-alia advantageous in order to allow a control of the diaphragm valve by applying fluidic pressure on the diaphragm such that a separate actuator can be omitted.

According to an embodiment of the present invention, the apparatus is a medical device configured to eject a medicament or the apparatus is a dispense interface attachable to a medical device configured to eject a medicament, wherein the diaphragm valve is configured to control fluid communication of a medicament contained in a reservoir of the medical device and a dose dispenser. For instance, the dose dispenser is a needle assembly attachable to the dispense interface or the medical device.

According to an embodiment of the present invention, the apparatus comprises at least two of the diaphragm valves and the medical device respectively comprises at least two of the reservoirs.

BRIEF DESCRIPTION OF THE DRAWINGS

These as well as other advantages of various aspects of the present invention will become apparent to those of ordinary skill in the art by reading the following detailed description, with appropriate reference to the accompanying drawings, in which.

DETAILED DESCRIPTION

Figure 1:
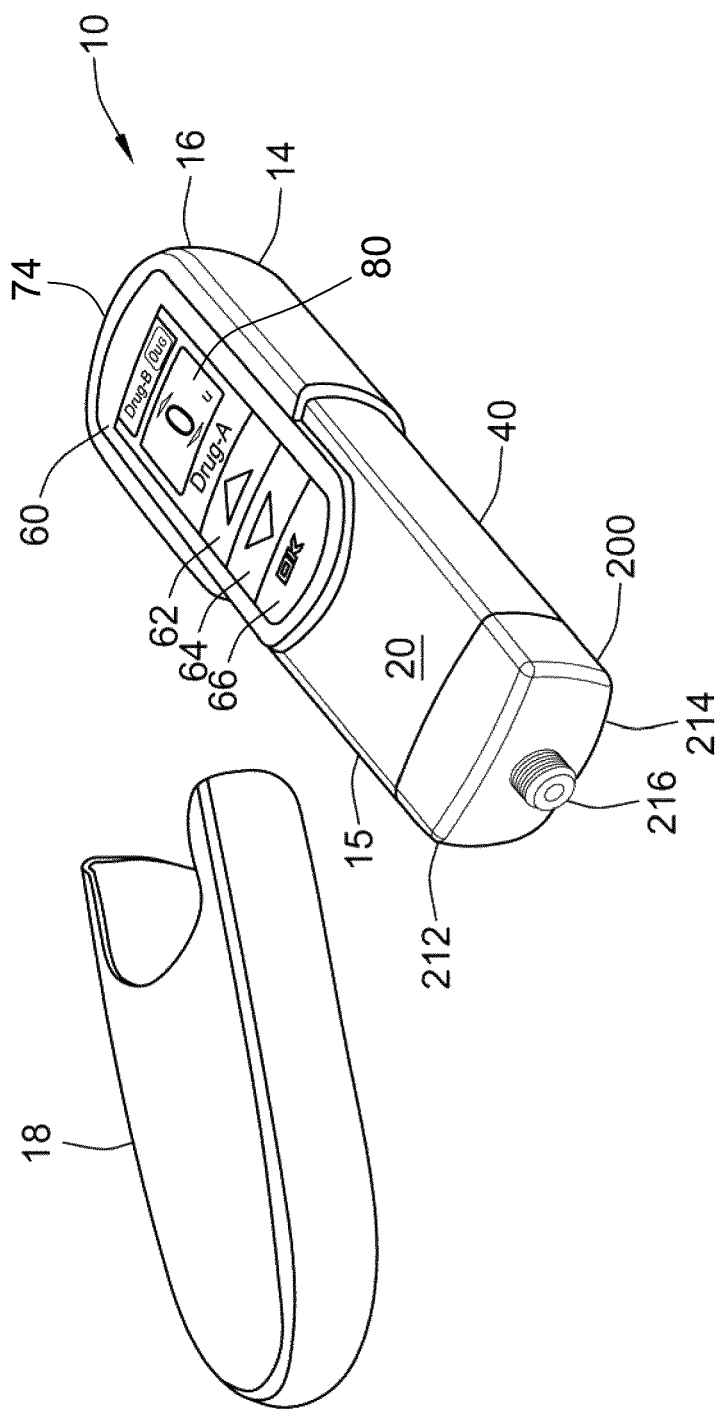
FIG. 1 illustrates a perspective view of the delivery device illustrated in FIG. 1a and 1b with an end cap of the device removed.
Figure 2:
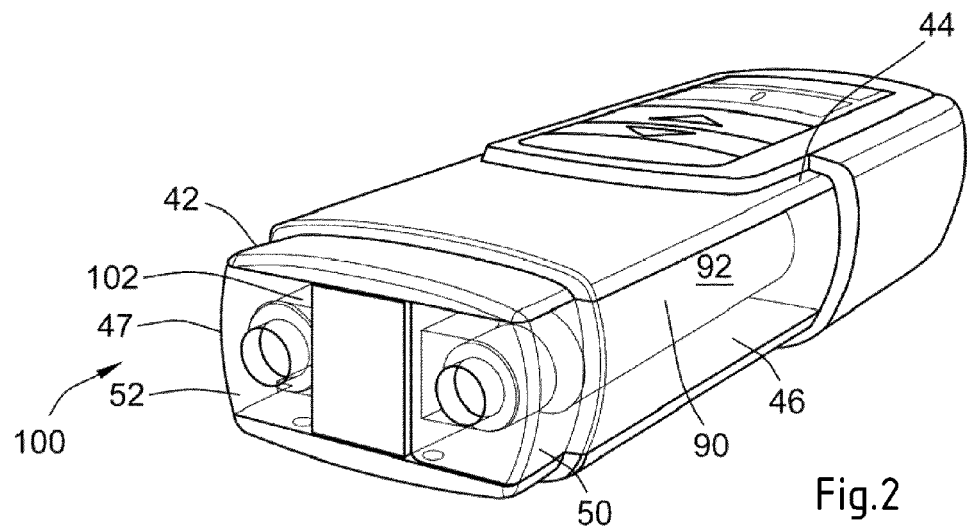
FIG. 2 illustrates a perspective view of the delivery device distal end showing the cartridge.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1).

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
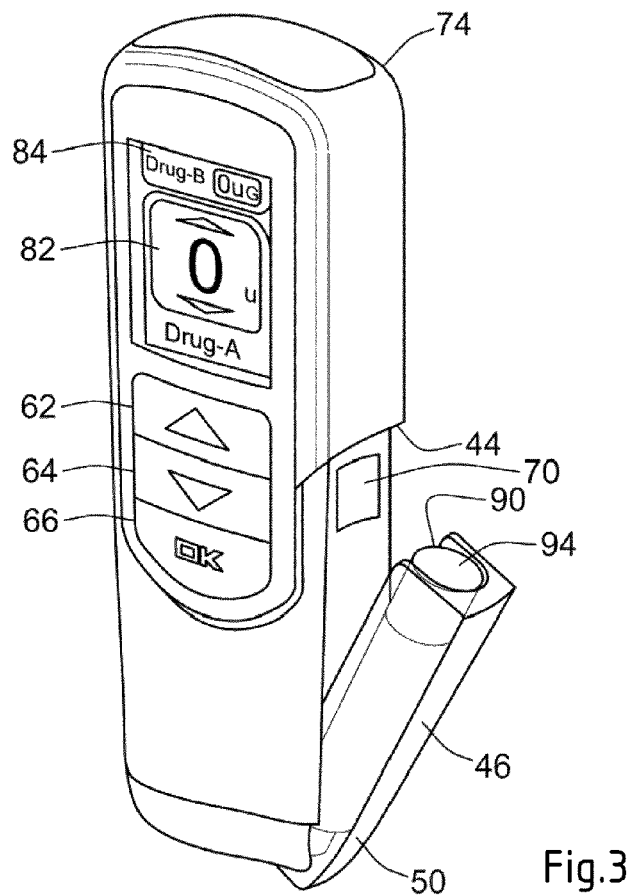
FIG. 3 illustrates a perspective view of the cartridge holder illustrated in FIG. 1 with one cartridge retainer in an open position.

As shown in FIG. 3, the first and a second cartridge retainers 50, 52 comprise hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
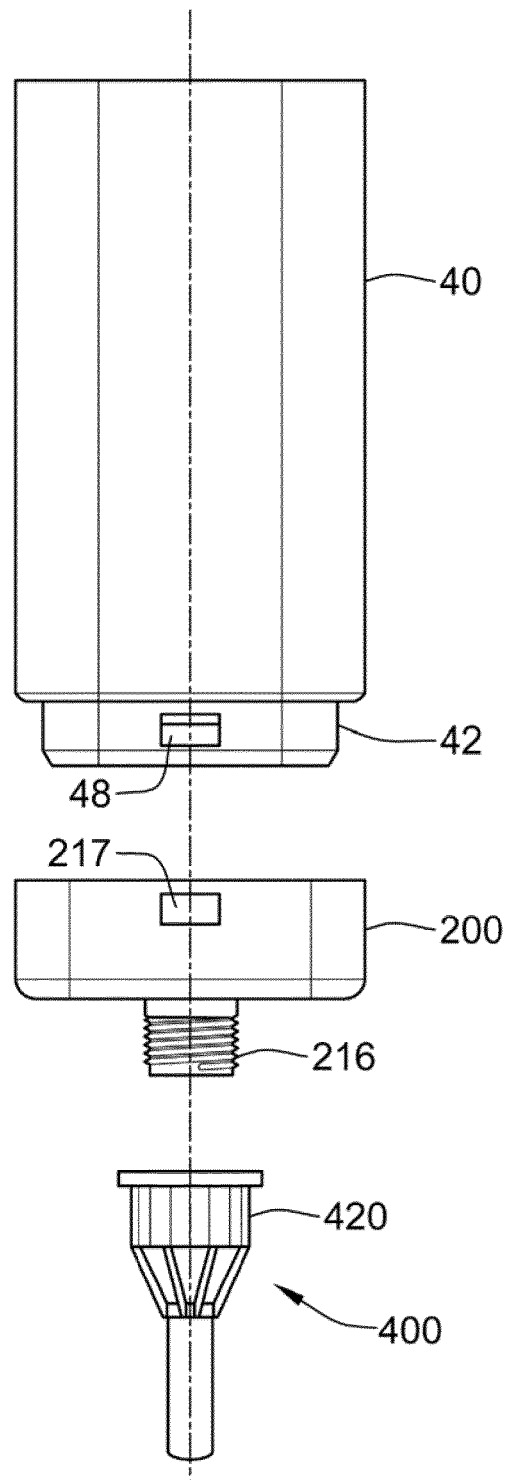
FIG. 4 illustrates a dispense interface and a dose dispenser that may be removably mounted on a distal end of the delivery device illustrated in FIG. 1.

As mentioned above when discussing FIG. 1, a dispense interface 200 is coupled to the distal end of the cartridge holder 40. FIG. 4 illustrates a flat view of the dispense interface 200 unconnected to the distal end of the cartridge holder 40. A dose dispenser or needle assembly that may be used with the interface 200 is also illustrated and is provided in a protective outer cap 420.

Figure 5:
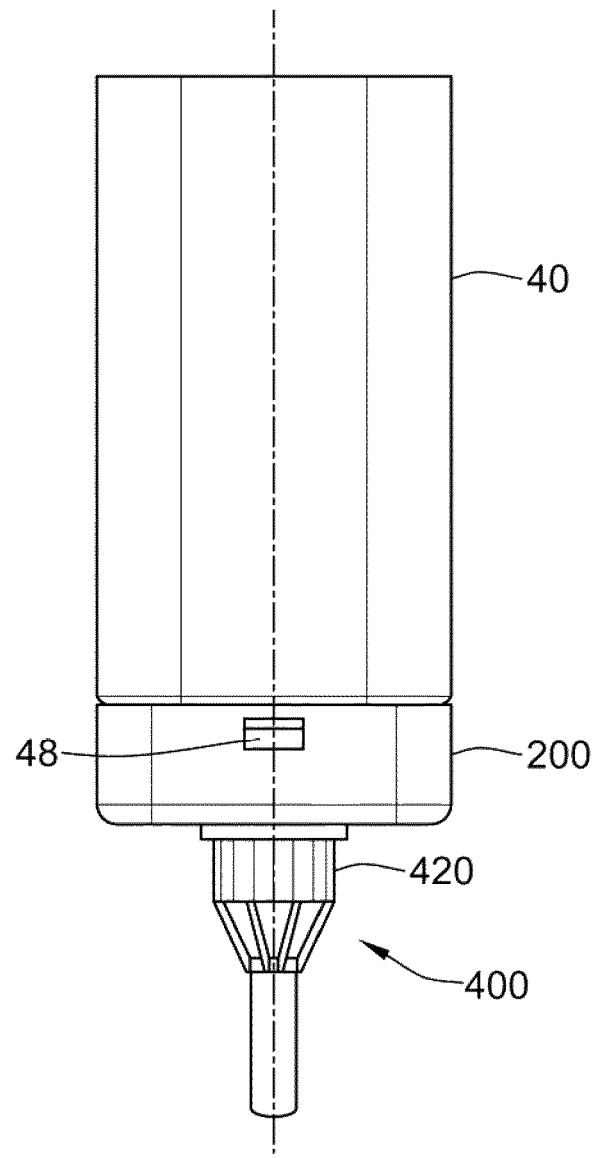
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
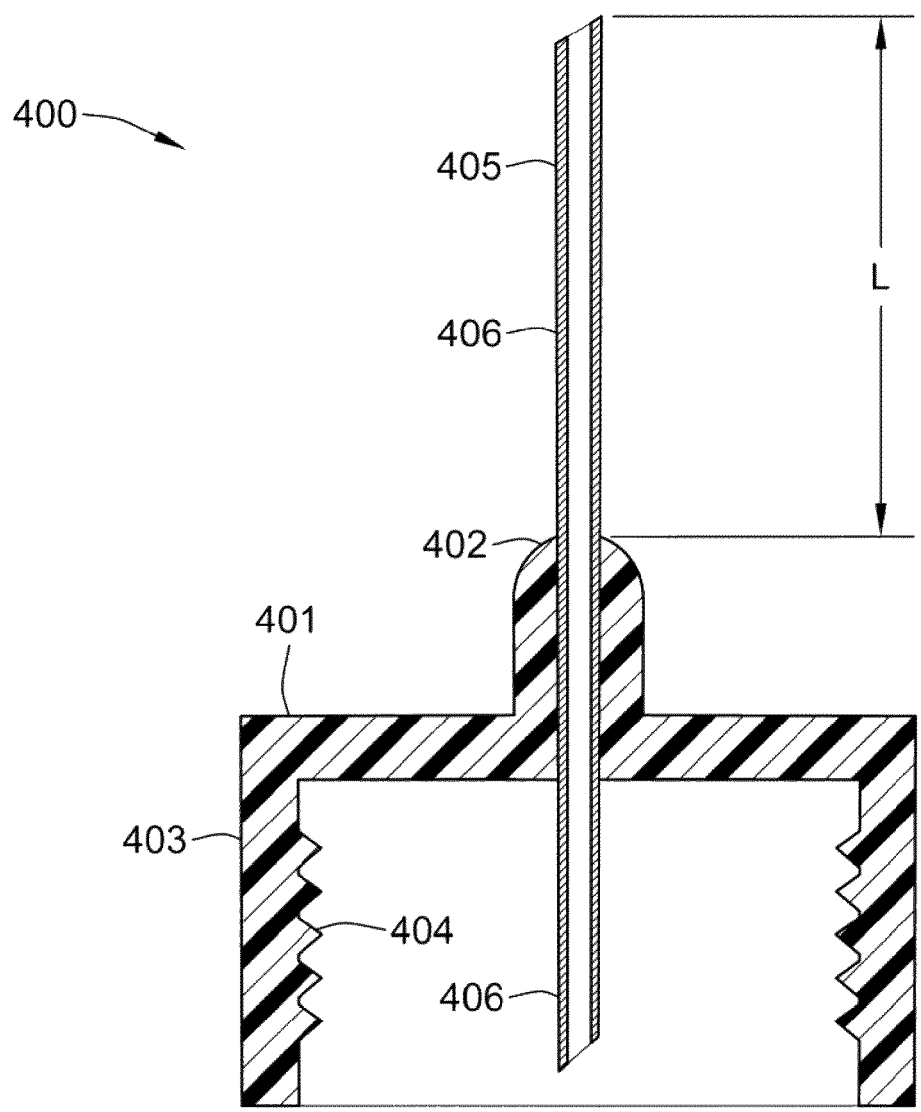
FIG. 6 illustrates one arrangement of the dose dispenser that may be mounted on a distal end of the delivery device.
Figure 7:
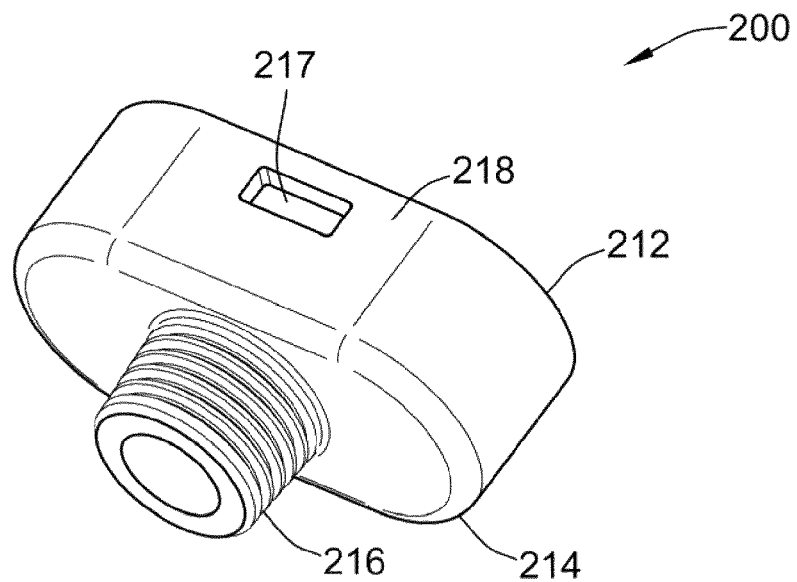
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 402 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 406 of the needle assembly 400 protrudes from an opposite side of the circular disc so that it is concentrically surrounded by the sleeve 403. In one needle assembly arrangement, the second or proximal piercing end 406 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:

a. a main outer body 210,
    b. an first inner body 220,
    c. a second inner body 230,
    d. a first piercing needle 240,
    e. a second piercing needle 250,
    f. a valve seal 260, and
    g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213a and a second rib 213b. This first rib 213a is also illustrated in FIG. 10. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224a and 224b are provided along an outer surface 222 of the first inner body 220.

Figure 8:
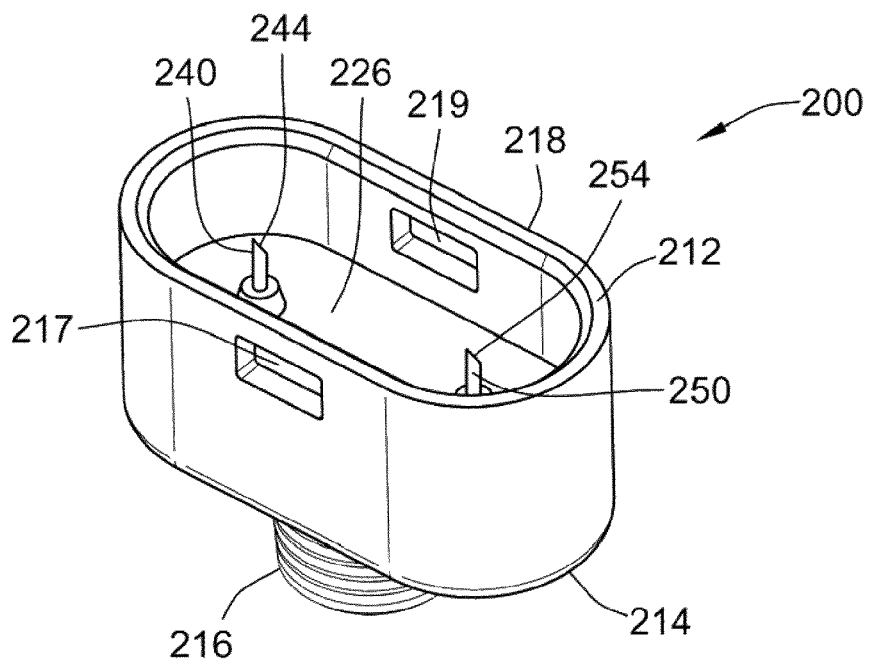
FIG. 8 illustrates another perspective view of the dispense interface illustrated in FIG. 4.
Figure 9:
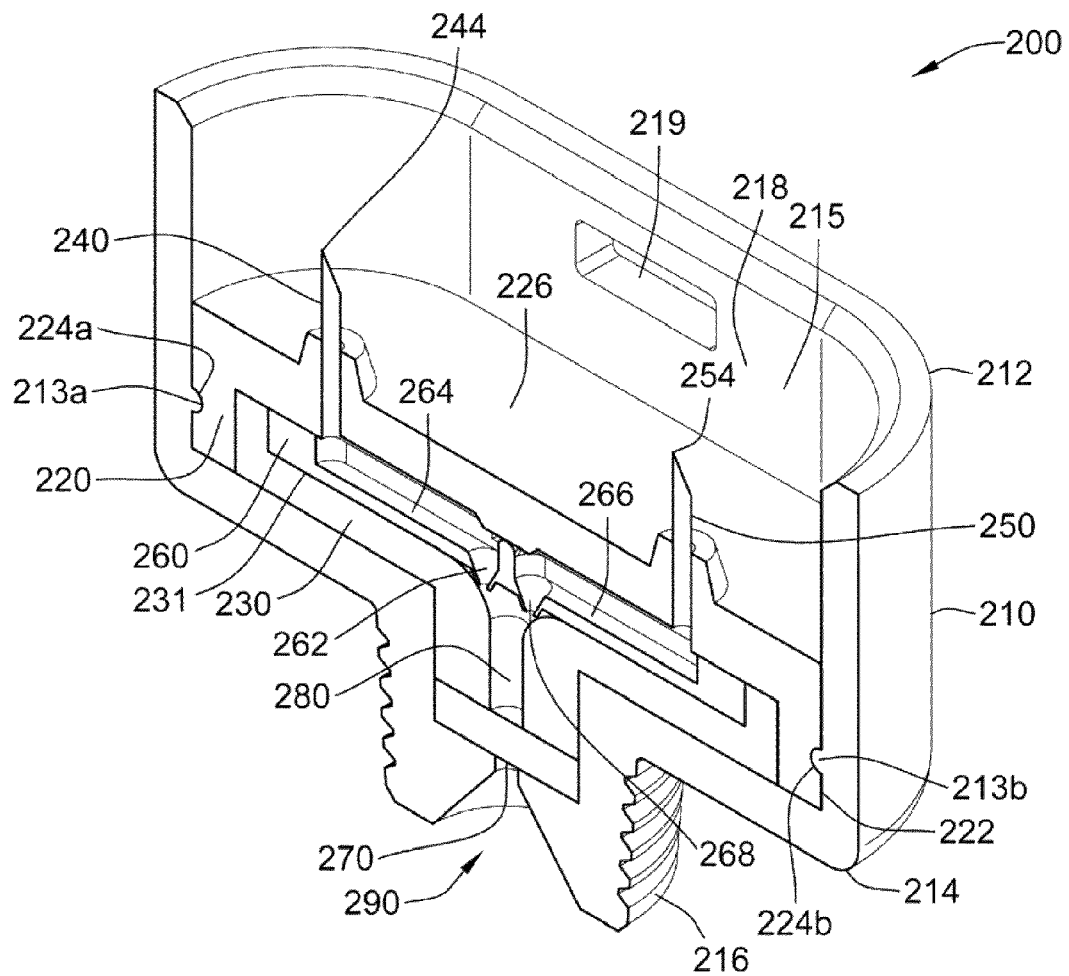
FIG. 9 illustrates a cross-sectional view of the dispense interface illustrated in FIG. 4.
Figure 10:
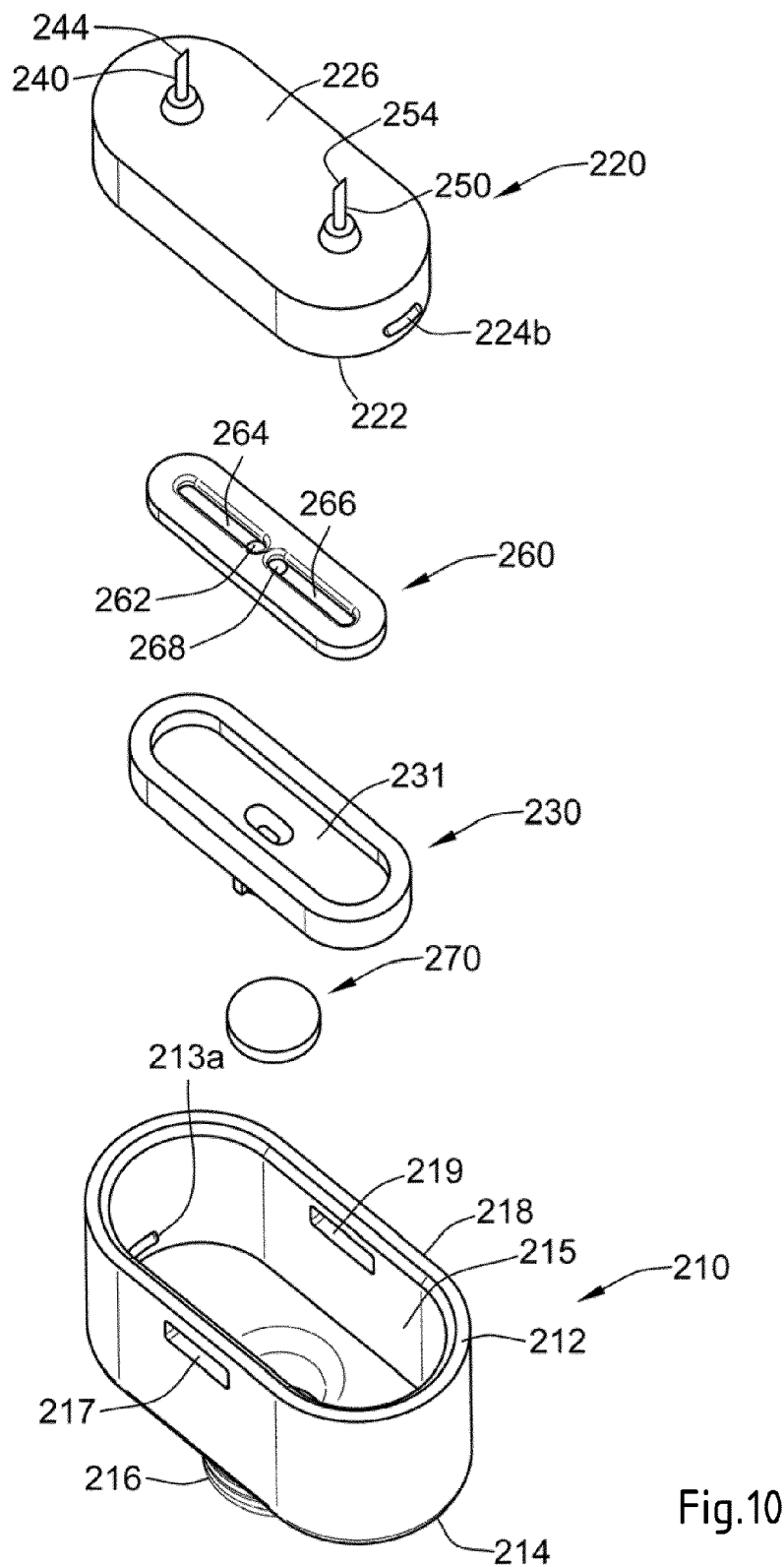
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
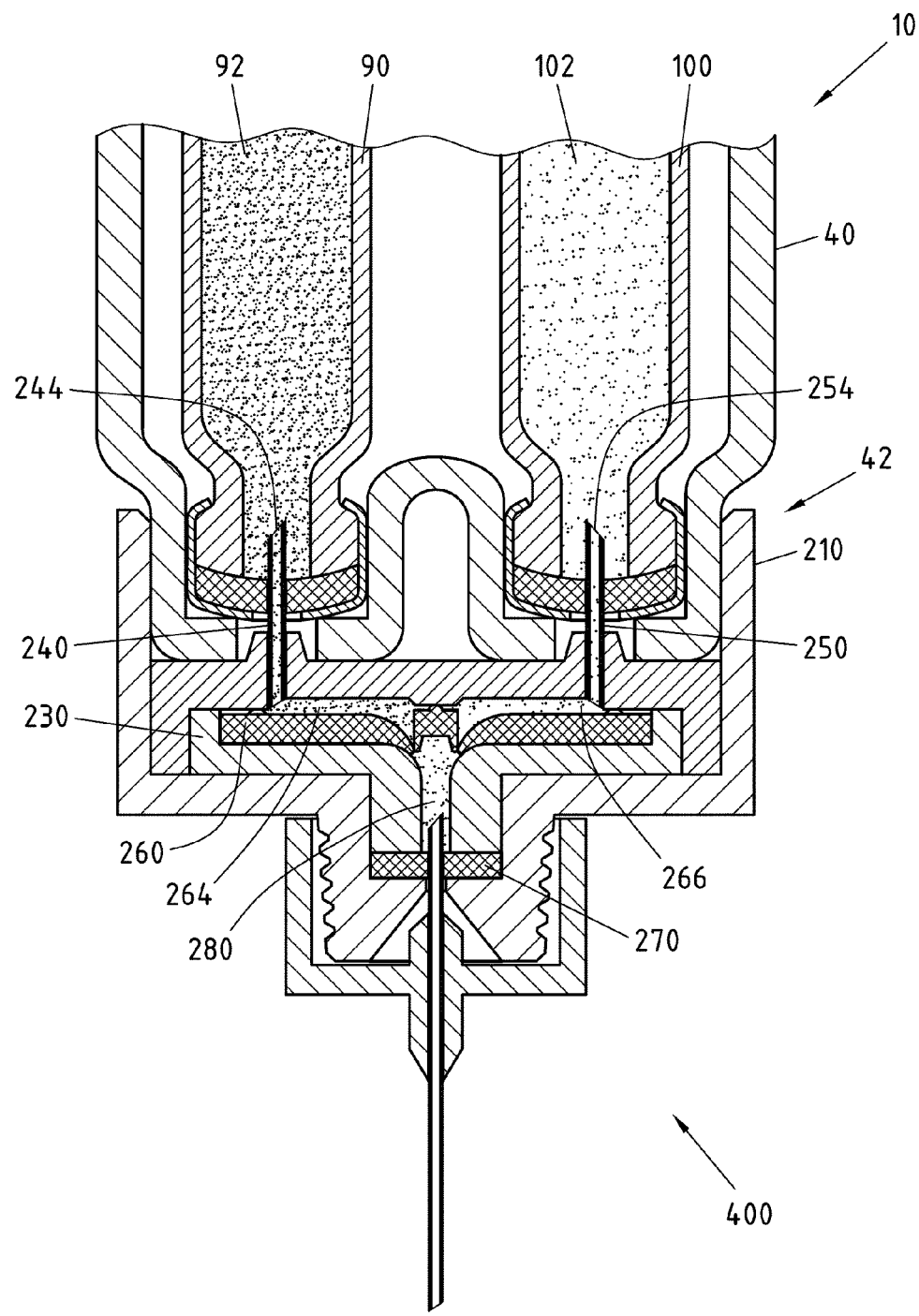
FIG. 11 illustrates a cross-sectional view of the dispense interface and dose dispenser mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

FIGS. 12 to 15 illustrate an embodiment of a dispense interface 2000 alternative to the embodiment of the dispense interface 200 illustrated in FIGS. 7 to 11. In FIGS. 12 to 15 the same reference signs as in FIGS. 7 to 11 are used for the same parts. Furthermore, at this point, it is mainly referred to the above description of the embodiment of the dispense interface 200 illustrated in FIGS. 7 to 11 and, basically, the differences are described only.

One exemplary difference between the dispense interface 200 and the dispense interface 2000 is the outer shape. In particular, the dispense interface 2000 is attachable to a drug deliver device by axial attachment means as described above and at least partially insertable in the drug delivery device. For instance, once the dispense interface 2000 is attached to the distal end of the drug delivery device, the distal end of the main body of the drug delivery device covers a portion of the dispense interface 2000.

Figure 12:
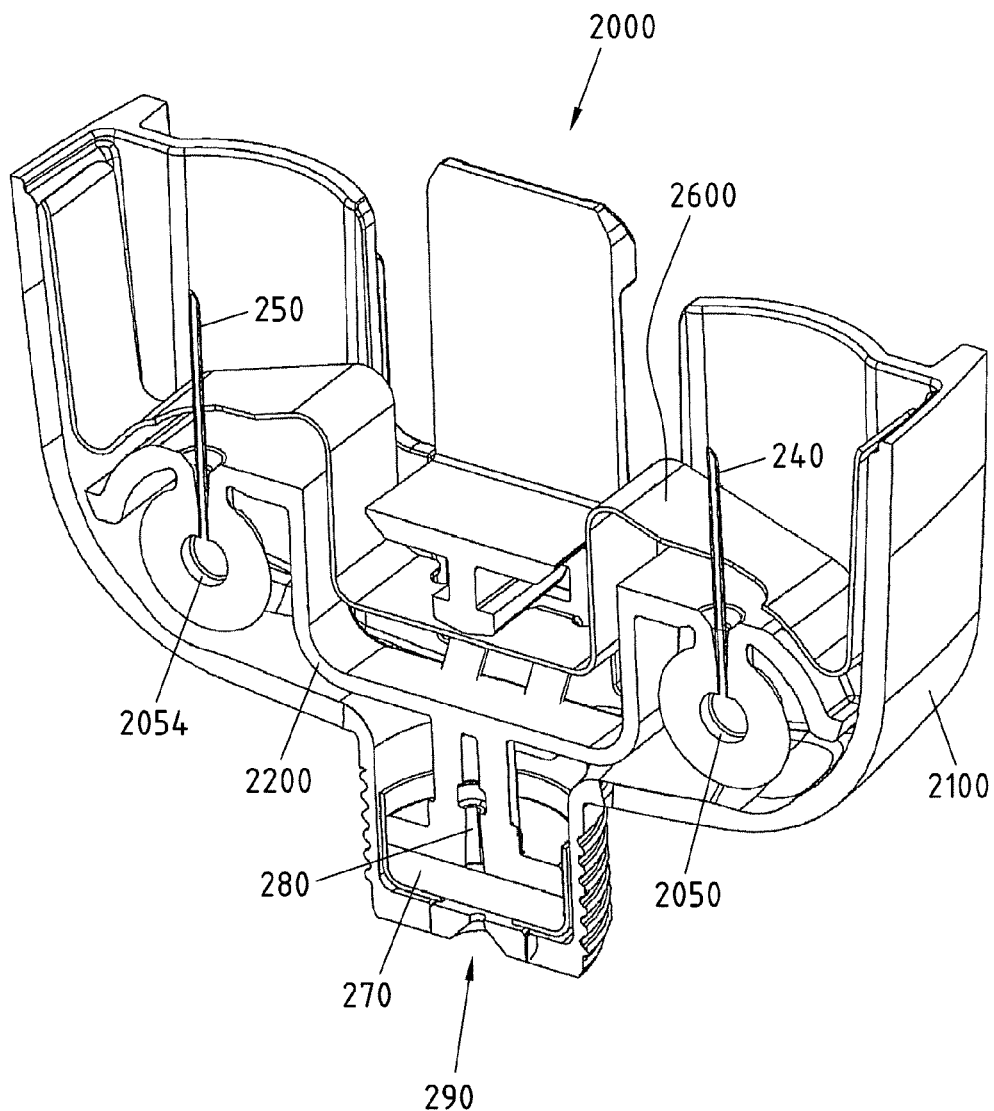
FIG. 12 illustrates a cross-sectional view of an alternative embodiment of a dispense interface.

As will now be discussed in greater detail, in one preferred arrangement, the dispense interface 2000 illustrated in FIGS. 12 to 14 comprises:
    a. a main outer body 2100;
    b. an inner body 2200;
    c. a manifold 2300;
    d. a first piercing needle 240;
    e. a second piercing needle 250;
    f. a lock-out spring 2600;
    g. a first diaphragm valve (e.g. diaphragm 2700);
    h. a second diaphragm valve (e.g. diaphragm 2750); and
    i. an outer septum 270.

Figure 14:
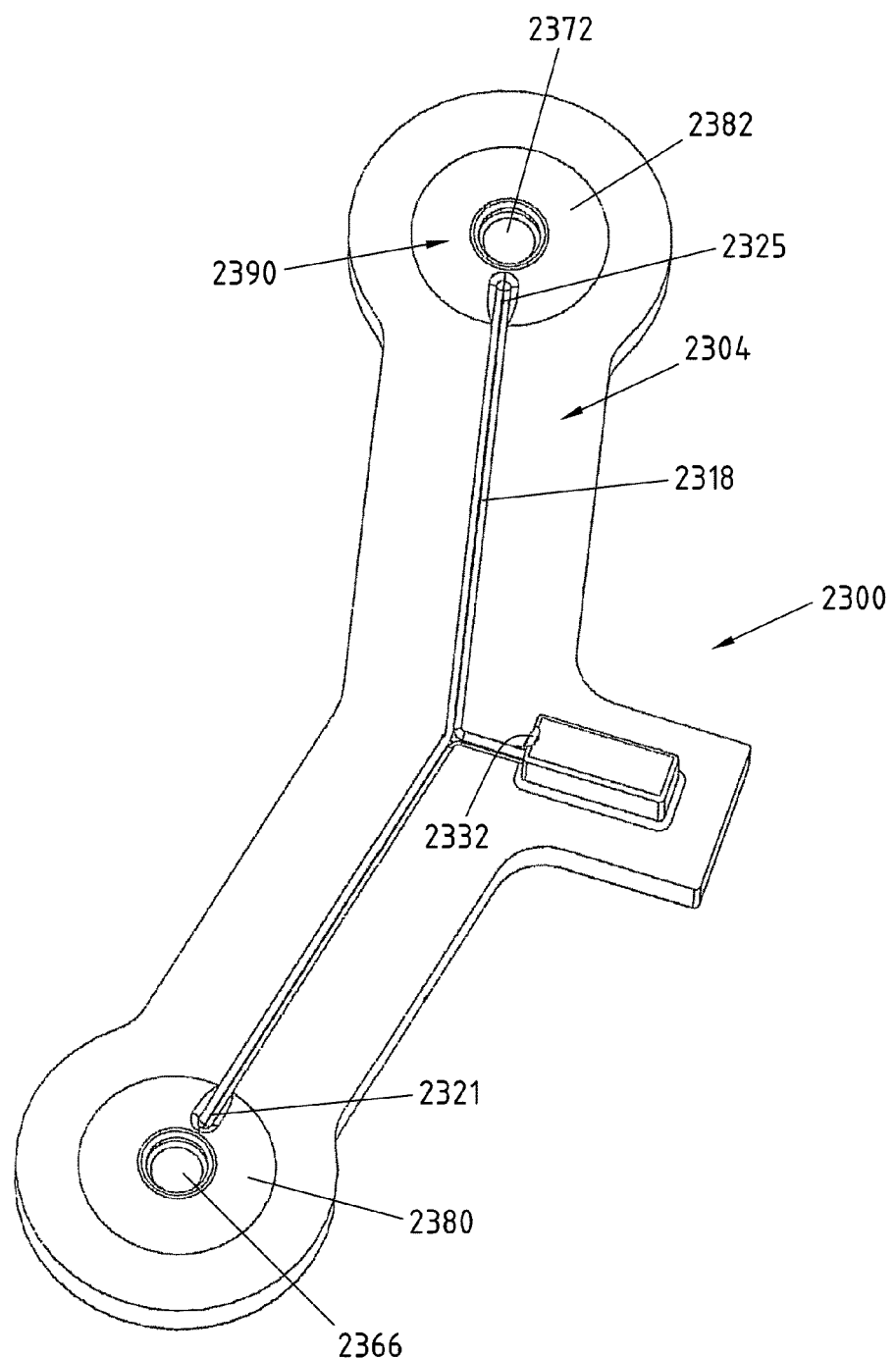
FIG. 14 illustrates a manifold of the alternative embodiment of a dispense interface illustrated in FIG. 12.

As illustrated in FIG. 14, the manifold 2300 comprises a first valve cavity 2366 and a second valve cavity 2372 provided along its top surface 2304. These cavities 2366, 2372 may be substantially circular. The first valve cavity 2366 is shaped for receiving a circular protrusion 2710 of a first diaphragm 2700. Similarly, the second valve cavity 2372 is shaped for receiving a circular protrusion 2760 of a second diaphragm 2750.

Figure 13:
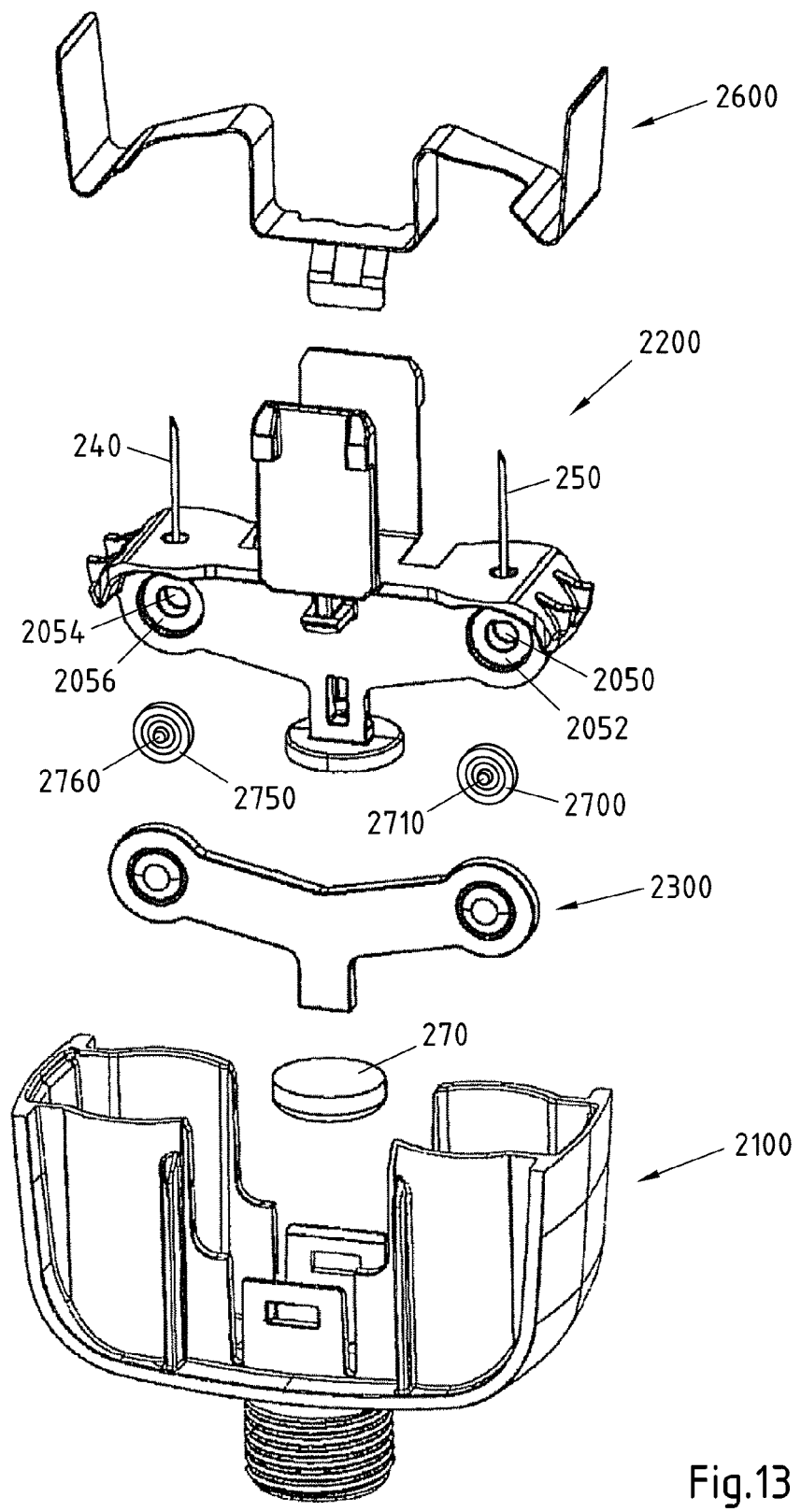
FIG. 13 illustrates an exploded of the alternative embodiment of a dispense interface illustrated in FIG. 12.

For example, in the exploded view illustrated in FIG. 13, alternative perspective views of both the first diaphragm 2700 and the second diaphragm 2750 are provided. As can be seen from these exploded views, the first diaphragm 2700 is substantially disc shaped and comprises a circular protrusion 2710 near the center of this disc shape. Similarly, the second diaphragm 2750 is substantially disc shaped and comprises a circular protrusion 2760 near the center of this disc shape.

Returning to the perspective view of the manifold 2300 provided by FIG. 14, preferably, the first valve cavity 2366 is positioned in the center of a first convex protrusion 2380 situated along the top surface 2304 of the manifold 2300. In such an arrangement, when the circular protrusion 2710 of the first diaphragm 2700 is seated within the first valve cavity 2366, the diaphragm 2700 provides a fluid seal between the first circular recess or reservoir 2050 defined by the inner body 2000 and the fluid groove arrangement 2318 provided along the surface 2304 of the manifold 2300. For instance, a rim of the diaphragm may be pressed on a set-back 2052 of the reservoir 2050 such that the diaphragm is in a pre-stressed state.

However, if fluidic pressure is applied upon the first diaphragm 2700 (e.g., during a dose priming or a dose injecting step), the first diaphragm 2700 may change from the pre-stressed state to an even more stressed state (which is below referred to as stressed state). For instance, the first diaphragm will change from the pre-stressed to the stressed state, if a fluidic pressure threshold is overcome. In the stressed state, fluidic pressure inverts the natural disc shape of the first diaphragm 2700 so that the surface of the first diaphragm inverts and thereby will reside along a top surface of the first convex protrusion 2380. In this stressed state, the first diaphragm 2700 will allow fluid to flow from the first reservoir of the inner body 2000 and the fluid groove arrangement 2318 of the manifold 2300. Accordingly, this arrangement is the first diaphragm valve.

Similarly, the second valve cavity 2372 is also shaped for receiving a circular protrusion 2760 of a second disc shaped diaphragm 2750. Moreover, this second valve cavity 2372 is also positioned near an apex of a second convex protrusion 2390. The second diaphragm valve operates in a similar manner as the first diaphragm valve when fluidic pressure is applied.

Figure 15:
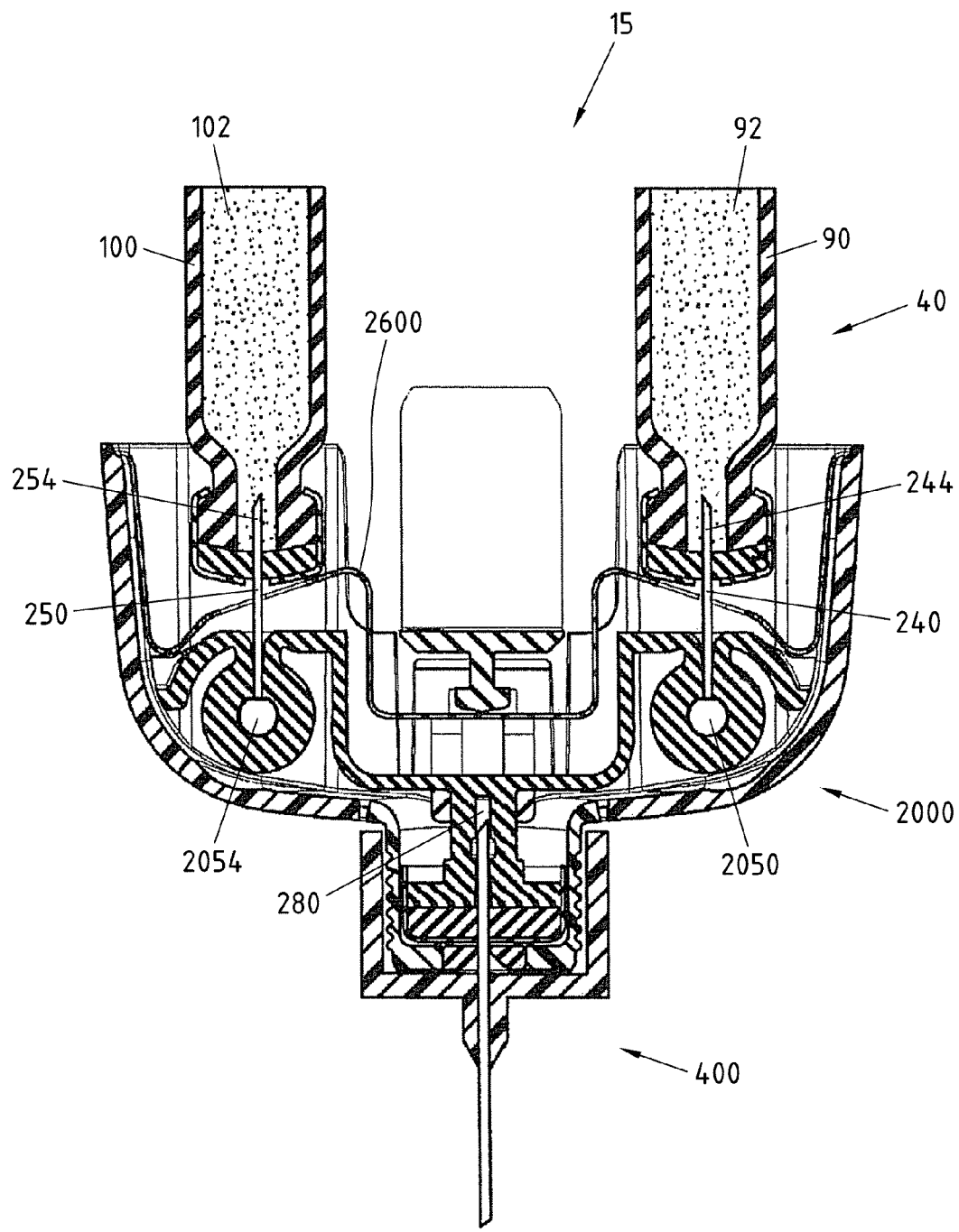
FIG. 15 illustrates a cross-sectional view of the alternative embodiment of a dispense interface illustrated in FIG. 12 and the dose dispenser mounted onto a drug delivery device, such as the device illustrated in FIG. 1.

FIG. 15 illustrates the dispense interface 2000 after it has been mounted onto the distal end of the cartridge holder 40 of a drug delivery device such as the drug delivery device 10 illustrated in FIG. 1. As illustrated, the needle assembly 400 is mounted to the distal end of the dispense interface 2000. Fluid flow will now be explained with respect to FIG. 15.

As illustrated in FIG. 15, the dispense interface 2000 is coupled to the distal end of a cartridge holder 40. This cartridge holder 40 is illustrated as containing the first cartridge 90 containing the primary medicament 92 and the second cartridge 100 containing the secondary medicament 102. Once coupled to the cartridge holder 40, the dispense interface 2000 essentially provides a mechanism for providing a fluid communication path from the first and second cartridges 90, 100 to the holding chamber 280 defined by the inner body 2200. This holding chamber 280 is illustrated as being in fluid communication with the needle assembly 400 (i.e. the double ended needle assembly 400). As illustrated, the proximal needle of the double ended needle assembly 400 is in fluid communication with the holding chamber 280.

The proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with the first reservoir 2050 defined by the inner body 2000.

Similarly, the proximal piercing end 254 of the second piercing needle 250 resides in fluid communication with the secondary medicament 102 of the second cartridge 100. A distal end of the second piercing needle 250 will also be in fluid communication with the second reservoir 2054 defined by the inner body 2000.

For instance, as pressure builds up in the first cartridge 90 and the second cartridge 100, fluidic pressure will build up in both the first and second piercing needles 240, 250. As such, the pressure will be built up in both the first and second reservoirs 2050, 2054 and this fluidic pressure will invert the first and second diaphragms 2700, 2750. For instance, a fluidic pressure threshold has to be overcome to invert the first and second diaphragm valves.

This inversion of the first diaphragm 2700 will allow the first medicament 92 to flow out of the first reservoir 2050, around the now inverted first diaphragm 2700 and then into the start point 2321 of the fluid groove 2318. Similarly, this inversion of the second diaphragm 2750 will allow the second medicament 102 to flow out of the second reservoir 100, around the now inverted second diaphragm 2750 and then into the start point 2325 of the fluid groove 2318. Under this continued pressure, the medicaments will then flow into the holding chamber 280 of the inner body 2200. Alternatively or additionally, the medicament may then flow out of the outlet 290 of the dispense interface 2000. The first and second medicaments may be administered at the same time so that the medicaments mix in the output fluid path or the holding chamber 280. Alternatively, the medicaments may be administered in a sequence. For example, the first medicament 92 may be administered first, and the second medicament may be administered after administration of the first medicament is finished. Thus, the medicaments don't mix in the device, or only to a small extent.

Figure 16A:
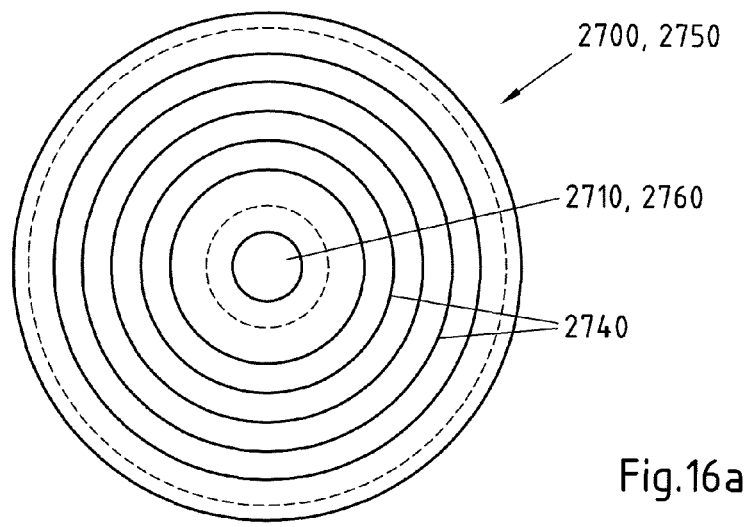
FIG. 16 illustrates an substantially disc shaped diaphragm having a wavelike flexible cross-sectional shape.
Figure 16B:
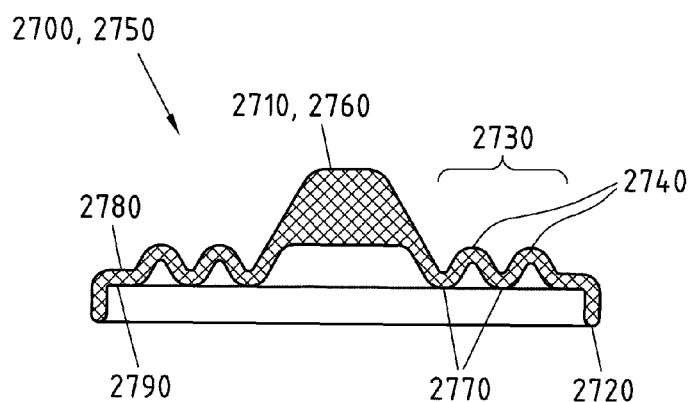

FIG. 16a to b illustrate the first and second diaphragm 2700, 2750. As illustrated, the diaphragm 2700, 2750 is substantially disc shaped. Alternatively, the diaphragm may be substantially convex shaped. It comprises a rim 2720 and a circular protrusion 2710, 2760 at the center of the diaphragm 2700, 2750. In the pre-stressed state the rim 2720 of the diaphragm 2700, 2750, for instance resides on the set-back 2052, 2056 of the reservoir 2050, 2054.

The diaphragm 2700, 2750 comprises a wavelike flexible cross-sectional shape 2730. This wavelike flexible cross-sectional shape 2730 interrupts the disc shape of the diaphragm 2700, 2750 and comprises one or more peaks 2740 and one or more throughs 2770. The peaks 2740 are arranged outside (i.e. above) the top surface plane 2780 of the disc shape and the throughs 2770 are arranged outside (i.e. below) the bottom surface plane 2790 of the disc shape. In the example embodiment of FIG. 16, the thickness of the material of the flexible cross-sectional shape 2730 equals the thickness of the material of the disc shape.

The wavelike flexible cross-sectional shape 2730 decreases the stiffness of the diaphragm 2700, 2750 compared to an uninterruptedly disc shaped diaphragm. Therefore, if the opening pressure threshold is for instance predefined, the wavelike flexible cross-sectional shape 2730 allows to make the diaphragm 2700, 2750 from a (biocompatible) material being more rigid than the material from which an uninterruptedly disc shaped diaphragm (e.g. FIG. 17) is to be made. The number of peaks and throughs may depend on the thickness, the diameter of the diaphragm and/or the stiffness of the material. For example, if the material is stiff, a higher number (for example more than three) peaks and throughs are used in order to provide a higher flexibility of the diaphragm 2700, 2750. In an example embodiment, the diaphragm 2700, 2750 comprises two peaks 2740 and two throughs 2770, as shown in FIGS. 16a and 16b.

Figure 17:
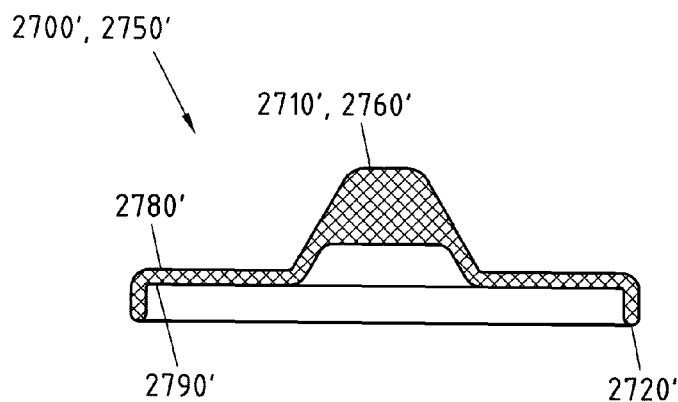
FIG. 17 illustrates an uninterruptedly disc shaped diaphragm.

FIG. 17 illustrates an uninterruptedly disc shaped diaphragm 2700', 2750'. It comprises a rim 2720' and a circular protrusion 2760' at the center of the diaphragm 2700', 2750'. The bottom and top surface 2780', 2790' of the disc shape are uninterruptedly formed.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)—NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)—NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)—NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A diaphragm valve comprising:
   first and second diaphragms, each diaphragm of said diaphragm valve is made from a substantially rigid thermoplastic material, each diaphragm having at least a partially flexible cross-sectional shape, wherein each diaphragm is configured to allow fluid flow if a fluidic pressure greater than a fluidic pressure threshold is applied on the diaphragm causing the flexible cross-sectional shape to invert;
   first and second convex protrusions of a manifold, wherein each convex protrusion houses a respective diaphragm; and
   first and second fluid grooves of the manifold, each having a respective start point, each start point being coupled to one of the two convex protrusions, and
   wherein the first and second fluid grooves are coupled to a holding chamber of the manifold,
   wherein each fluid groove is configured to allow fluid to flow from the diaphragms of the convex protrusions to the holding chamber when the diaphragm is in an inverted state, and wherein the holding chamber is configured to mix the fluids from the two start points of the fluid groove.

2. The diaphragm valve according to claim 1, wherein said flexible cross-sectional shape is configured to decrease a second moment of area of said diaphragm.

3. The diaphragm valve according to claim 1, wherein a thickness of said substantially rigid material varies at least in said flexible cross-sectional shape.

4. The diaphragm valve according to claim 1, wherein said flexible cross-sectional shape is at least partially wavelike.

5. The diaphragm valve according to claim 4, wherein said at least partially wavelike flexible cross-sectional shape comprises at least one through and/or one peak.

6. The diaphragm valve according to claim 1, wherein said diaphragm is convex shaped.

7. The diaphragm valve according to claim 1, wherein said diaphragm is rotationally symmetric.

8. The diaphragm valve according to claim 7, wherein said flexible cross-sectional shape is arranged between a rim of said diaphragm and a center of said diaphragm.

9. The diaphragm valve according to claim 1, wherein an outer diameter of said diaphragm is equal to or less than 1 cm.

10. The diaphragm valve according to claim 1, wherein a Young's modulus of said substantially rigid material is not less than 100 N/mm$^2$.

11. The diaphragm valve according to claim 1, wherein said substantially rigid material is one of semi-crystalline thermoplastics and amorphous thermoplastics.

12. The diaphragm valve according to claim 1, wherein said substantially rigid material is one of low density polyethylene and polytetrafluoroethylene.

13. The diaphragm valve according to claim 1, wherein said diaphragm valve is configured to enable fluid flow, if a fluidic pressure threshold is applied on said diaphragm valve.

14. The diaphragm valve according to claim 13, wherein said diaphragm valve is a component of a medical device configured to eject a medicament via an injection needle or said diaphragm valve is a dispense interface attachable to a medical device configured to eject a medicament via an injection needle, and wherein said diaphragm valve is configured to control fluid communication of a medicament contained in a reservoir of said medical device and a dose dispenser.

15. The diaphragm valve according to claim 1, wherein said holding chamber is configured to received fluid that has passed from two of said diaphragms.

* * * * *